(12) United States Patent
Hansen et al.

(10) Patent No.: US 6,413,786 B1
(45) Date of Patent: *Jul. 2, 2002

(54) BINDING ASSAYS USING OPTICAL RESONANCE OF COLLOIDAL PARTICLES

(75) Inventors: W. Peter Hansen; Petra Krauledat, both of Canaan, NY (US)

(73) Assignee: Union Biometrica Technology Holdings, Inc., NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/372,444

(22) Filed: Aug. 11, 1999

Related U.S. Application Data

(63) Continuation-in-part of application No. 08/789,211, filed on Jan. 23, 1997, now Pat. No. 5,939,021.
(60) Provisional application No. 60/096,159, filed on Aug. 11, 1998.

(51) Int. Cl.[7] .............................................. G01N 33/553
(52) U.S. Cl. ................... 436/526; 436/501; 436/518; 436/525; 436/527; 436/805; 436/808; 435/6; 435/283.1; 435/287.2; 435/975; 422/50; 422/55; 422/41; 422/82.05; 422/82.09; 356/301; 356/302; 356/303; 356/319; 356/322; 356/336; 356/339; 356/128
(58) Field of Search ................... 436/518, 526, 436/501, 525, 527, 805, 808; 435/283.1, 6, 287.2, 975; 422/50, 55, 41, 82.05, 82.09; 356/301, 302, 303, 319, 322, 336, 339, 128

(56) References Cited

U.S. PATENT DOCUMENTS 4,313,734 A * 2/1982 Leuvering .................... 23/230
5,939,021 A * 8/1999 Hansen et al. ................ 422/55

FOREIGN PATENT DOCUMENTS

| WO | WO 98/10289 | 3/1998 |
| WO | WO 98/33070 | 7/1998 |
| WO | WO 98/37417 | 8/1998 |
| WO | WO 99/01766 | 1/1999 |

OTHER PUBLICATIONS

AE A copy of the PCT Search Report.

* cited by examiner

Primary Examiner—Christopher L. Chin
Assistant Examiner—Pensee Do
(74) Attorney, Agent, or Firm—Crosby, Heafey, Roach & May LLP

(57) ABSTRACT

A device and a method enable the rapid, quantitative evaluation of a large collection of ligands for binding affinity with a certain immobilized receptor, the improvements being that binding pan be detected without the need for a label and that binding is carried out in solution phase at a high rate. The instrument has at least two embodiments, one is based on a sensitive absorption photometer and the other on a sensitive light scatter photometer operating at a specific resonance wavelength, $\lambda_R$, of small, metallic, colloidal particles. The resonance is present in small particles having a complex refractive index with real part $n(\lambda)$ approaching 0 and imaginary part $k(\lambda)$ approaching $\sqrt{2}$ simultaneously at a specific wavelength $\lambda_R$. The particles are substantially spherical and substantially smaller than $\lambda_R$. The receptor is immobilized on a suspension of such particles and ligand binding is detected by a change in optical absorption or light scatter at the resonance wavelength.

1 Claim, 7 Drawing Sheets

BINDING ASSAYS USING OPTICAL RESONANCE OF COLLOIDAL PARTICLES

The present application is based on Provisional Application No. 60/096,159 entitled "Binding Assays By Means Of Optical Resonance Of Colloidal Particles" filed on Aug. 11, 1998 and claims priority from that application; the present application is also a continuation in part of application Ser. No. 08/789,211 now U.S. Pat. No. 5,939,021 entitled "Homogeneous Binding Assay" filed on Jan. 23, 1997 and incorporated herein by reference.

BACKGROUND OF THE INVENTION

1. Field of the Invention

The present application concerns the field of detection of ligand binding and more specifically pertains to high-speed instruments for automatically screening large numbers of potentially therapeutic compounds by measuring their relative binding affinity for various biological receptors.

2. Description of Related Art

The methods of genetic engineering have been successful in identifying the genetic sequence of disease-related cell surface receptors and artificially expressing these receptors in substantial quantity and in purified form. Such receptors can also be isolated from cell preparations. Combinatorial chemistry techniques provide rapid synthesis of low molecular weight compounds that are potential binding partners for isolated or identified receptors. Once created, these vast libraries of compounds must be screened for relative binding affinity to the target receptor. High speed machinery has become essential for type of testing or screening to be accomplished in a timely fashion.

The traditional approach to screening has been to label each compound, for example, with a radioactive moiety, a fluorescent tag, or a luminescent tag and to then determine binding of the labeled compound to the receptor of interest. For this purpose receptor is generally immobilized and the labeled compound is allowed to contact the receptor. After a period of time, unbound compound is washed away and the immobilized receptors are analyzed for the presence of the bound label.

There are at least two problems in this approach. First, washing tends to disrupt weak binding that may be important for detecting compounds with some but not ideal activity. Second, the task of labeling an entire library of perhaps hundreds of thousands of compounds presents a practical limit to the number of compounds that can be screened. Each compound presents a unique problem to be solved for labeling, and not all can be labeled by the same tag. Finally, the presence of the label can modify the affinity between the compound and the receptor.

Therefore, it would be highly desirable to have an instrument and a method that eliminates labeling and yet allows the quantitative analysis of the binding affinity between a compound and a receptor. This would remove a fundamental limit to high speed screening of very large libraries of compounds.

The present invention achieves this goal by providing an instrument and a method that detects a change in the optical characteristics of the solid support to which the receptor has been bound when the receptor is occupied by an unlabeled binding compound. The solid support is a specific type of colloidal particle of less than 100 nm in diameter. This small size means that the binding kinetics for the reaction are similar to solution phase kinetics. The instrument automatically mixes the compound and the colloidal suspension of receptors, incubates the mixture, then reads the result at the rate of thousands of tests per hour.

In the copending application referenced above the present inventors discovered that optical resonance could be used to detect the crosslinking of particles. The current invention is not dependent on crosslinking of particles. As developed below, the present invention directly detects the binding of an unlabeled ligand to a particle.

SUMMARY OF THE INVENTION

The invention utilizes a specialized type of optically sensitive, sub-micron particle, the surface of which is pre-coated with a monolayer of a specific molecular receptor that can bind solution phase ligands (In this invention, "receptor" refers to a molecule immobilized on the particle that is capable of binding other molecules that are in free solution. Furthermore, in this invention, the molecules in free solution are termed "ligands"). The particle itself is a transducer that directly senses the binding of ligands to the receptor and creates an optical signal indicative of this binding. The particle itself is the binding sensor, thereby obviating the need to label the ligand.

The signal transduction properties of the particles used in the invention depend upon there being an optical light scatter and absorption resonance at a specific resonance wavelength $\lambda_R$. Such a resonance is present in small particles having a complex refractive index wherein a real part $n(\lambda)$ of the index approaches 0 while an imaginary part $k(\lambda)$ approaches $\sqrt{2}$ simultaneously at the specific wavelength $\lambda_R$. (In this invention a small particle is one that is less than approximately one tenth the wavelength of the incident light.) It is known from detailed theories of light scatter, that, when the above resonance condition is met, both light scatter and absorption are substantially greater than predicted by the Rayleigh theory of simple light scatter where it is assumed that n and k are constant and not functions of $\lambda$ (Bohrens and Huffman). The present invention demonstrates the additional surprising result that the intensity of small particle light scatter and absorption at the resonance wavelength changes when ligands bind to receptors immobilized on such resonant particles. The closer the two conditions of n and k are met, the stronger is the resonance, and the more sensitive the receptor-coated particles are to ligand binding.

Normally, expressions for light scatter and absorption from small particles with constant refractive indices are simple functions of wavelength. Generally speaking, both light scatter and absorption are highest for short wavelengths (e.g. for ultra-violet light) and lowest for long wavelengths (e.g. red or infrared light). This wavelength dependence is monotonic, meaning that there is a continuous progression from intense absorption and scatter at short wavelengths to less intense absorption and scatter at long wavelengths. Exceptions to this behavior occur for particles with a complex refractive index that has strong wavelength dependence.

If the refractive index of the particle varies with wavelength in such a way that the two conditions; 1). $n(\lambda)$ approaches 0 and 2). $k(\lambda)$ approaches $\sqrt{2}$ are simultaneously met at a specific wavelength $\lambda_R$, then light scatter and absorption increase dramatically in a narrow wavelength band around $\lambda_R$. This departure is termed a resonance. The resonance is delicate, and can be perturbed by the deposition of chemical agents on the surface of the particle. When a layer of receptors is coated onto the particle, the resonance is altered; but it is a surprising and important aspect of the present invention that when ligands then bind to the receptor layer, there is a further perturbation of the resonance that can be readily detected optically.

The optical signal pertaining to this invention is detected either by absorption or light scatter photometry. The optical resonance increases the level of light scatter and absorption by at least a factor of ten above the normal levels of light scatter at the resonance wavelength $\lambda_R$. This enables the optical detection of particles that are as small as the order of 100 Ångstroms (10 nm) at low concentrations. Such small particles advantageously diffuse virtually as rapidly as macromolecules in solution. Such rapid particle motion coupled with an interparticle spacing that is of the order of micrometers ($\mu$m) means that the ligand receptor surface binding reaction occurs at nearly maximal rates. Such particle-based reactions should be contrasted to binding reactions that occur on flat surfaces such as when receptors are immobilized on the surface of micro-wells. There the ligand must diffuse over distances of about a millimeter (1000 $\mu$m) or more to reach the receptor. These latter reactions are slow and impede the desired high throughput of an automated system for binding reaction screening.

The binding reactions and signal transduction in the present invention occur in a single, rapid step. This enables binding assays to be easily automated and carried out at such system throughput rates that large collections of ligands and receptors can be evaluated for binding affinity in relatively short periods of time by machines that run continuously and benefit from low complexity fluid handling mechanisms.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide a method and device for detecting the binding of unlabeled ligand to optically resonant colloidal particles.

Figure 1:
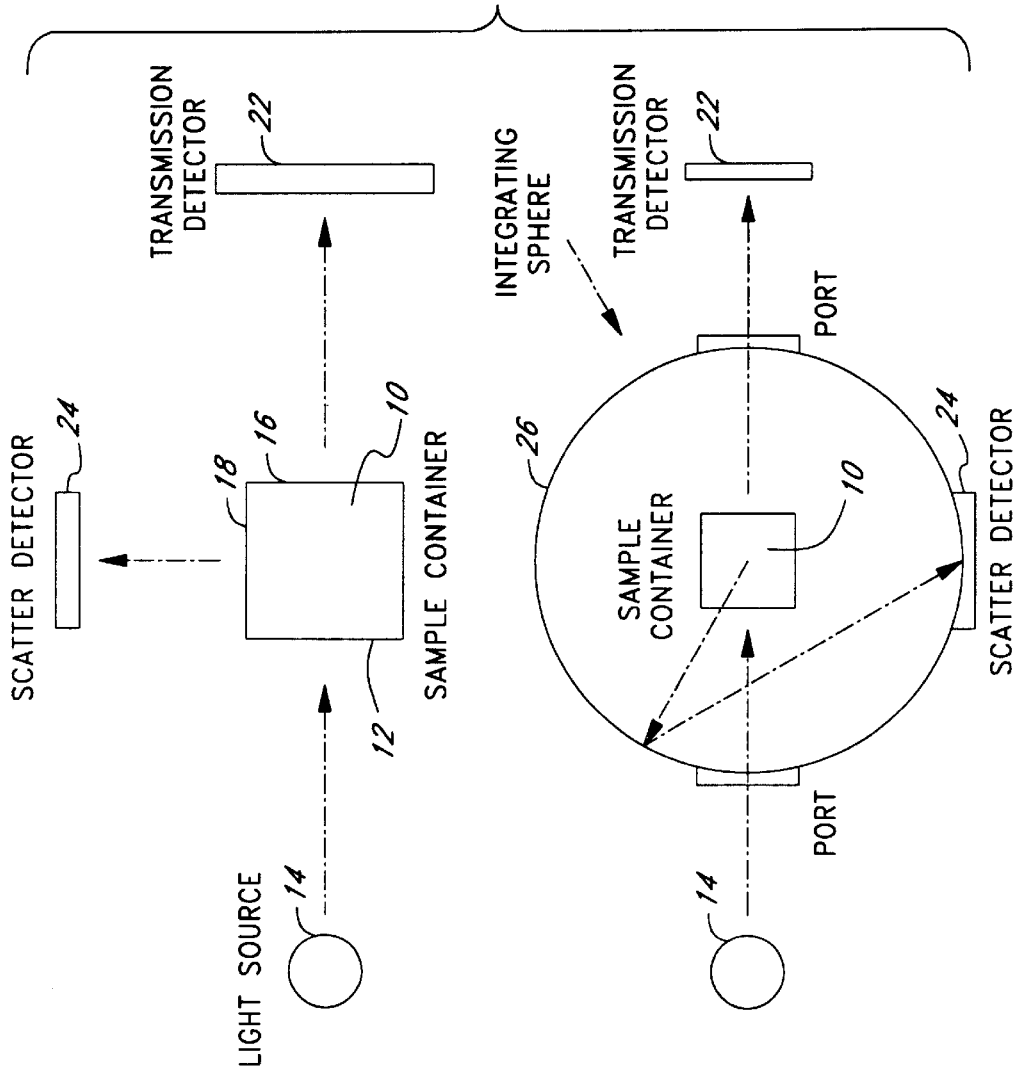
FIG. 1. represents a schematic of light scatter and light absorption detection.

Referring to FIG. 1, there is a container 10 for the liquid elements of the reaction mixture includes a window 12 for the admission of light from a light source 14 and a second set of windows 16, 18 through which transmitted and scattered light, respectively, can pass to a detector or set of detectors 22, 24. In one embodiment, the container is a well in a multi-well titer tray and in an alternative embodiment the container is a cuvette such as is employed in optical spectrophotometers. One embodiment of the device uses an integrating sphere 26 to integrate the scattered light which is sample through a port in the sphere 26. Other ports allow illumination of the sample container 10 and measurement of the transmitted light by the transmission detector 22.

Figure 2:
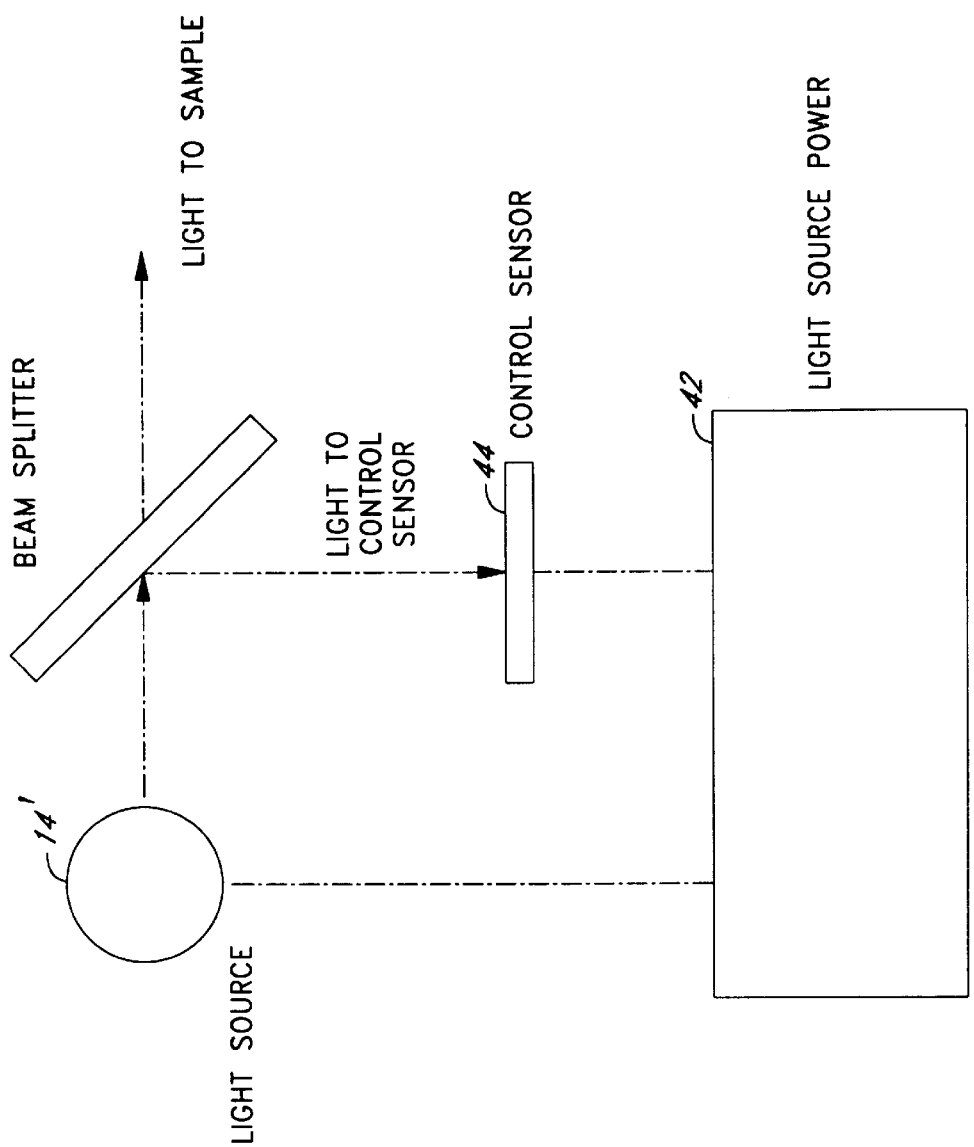
FIG. 2. shows a schematic diagram of light source stabilization used in the present invention.

The measurement of light transmission can be carried out by comparing a sample signal with a reference signal. The sample signal is obtained by measuring light transmitted through the sample at or near the resonance wavelength, $\lambda_R$. The reference signal is derived in one of two ways. Either it comes from light transmitted through the sample at wavelengths well outside the resonant band at $\lambda_R$ or from light transmitted through another well containing particles at the same concentration as the reaction mixture but lacking the ligand (e.g., a control mixture). Most commonly some sort of optical chopper or, alternatively, an optical beamsplitter is used to derive the sample and reference beams from a single light source. These approaches are important when the reacting mixture contains colored components that could make the relatively small resonance signal hard to detect without such a dual beam approach. As shown in FIG. 2 the light source 14 used for these measurements is best stabilized. A particularly useful light source is provided by a light emitting diode (LED) 14' that can be directly electrically modulated by a light source power module 42 in response to a feedback signal from a detector 44 that monitors light at $\lambda_R$ that has not passed through the reaction well.

Figure 3:
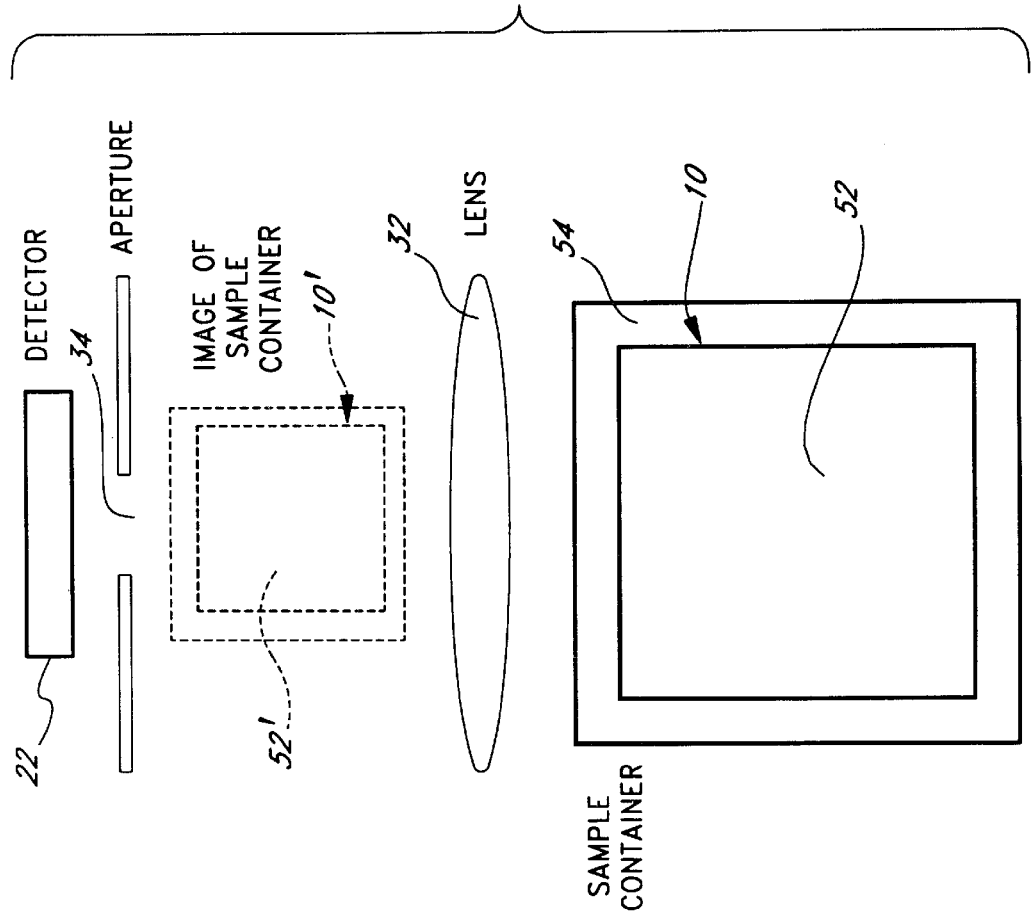
FIG. 3. illustrates the use of optical imaging to minimize background scattered light.

FIG. 3 shows a useful optical arrangement for avoiding unwanted background signals. A lens 32 images the liquid interior 52 of the reaction chamber 10 onto the surface of an optical detector 22. In this way the walls 54 of the container 10, which tend to scatter fight and produce an unwanted background, are defocused and the background light from the walls can be reduced with field stops and/or an aperture 34.

Figure 4:
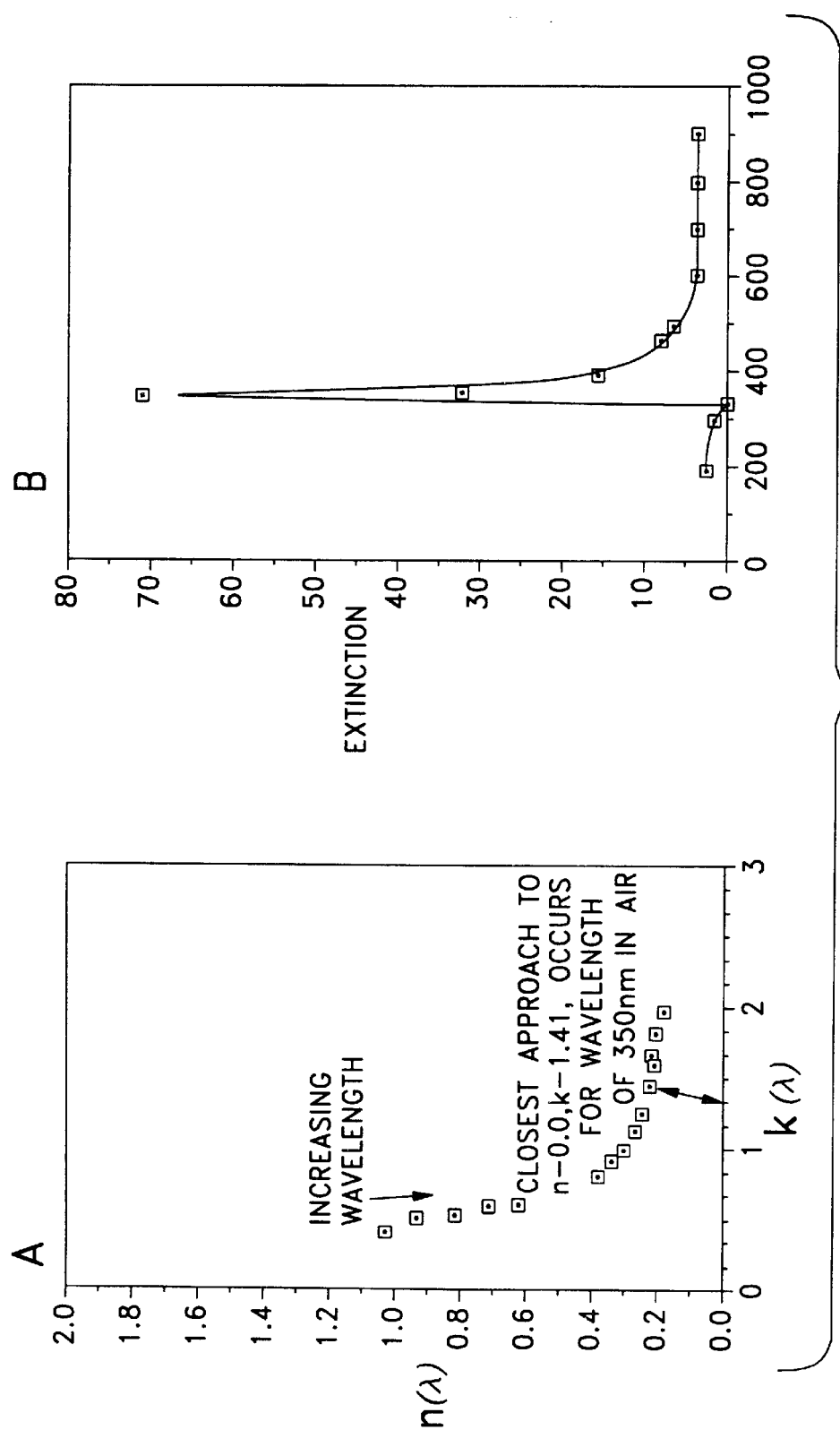
FIG. 4. is a parametric plot of k versus n for silver showing the effect of resonance on light extinction.

In this example resonant particles were prepared from silver colloids, such as can be purchased from British Biocell, International, Cardiff, U.K. Small, silver particles exhibit an optical resonance in the violet region of the spectrum. FIG. 4A shows a plot of $n(\lambda)$ and $k(\lambda)$ that illustrates that $n(\lambda)$ approaches 0 and $k(\lambda)$ approaches $\sqrt{2}$ at $\lambda_R$=390 nm ( FIG. 4B) when the particles are in vacuum. When the particles are immersed in water, the resonance is perturbed and shifted to a longer wavelength near 400 nm. Such resonant behavior is not seen in macroscopic silver material, it is only seen with small particles of silver where the particle boundaries are separated by distances that are small compared to the wavelength of the incident light.

Figure 5:
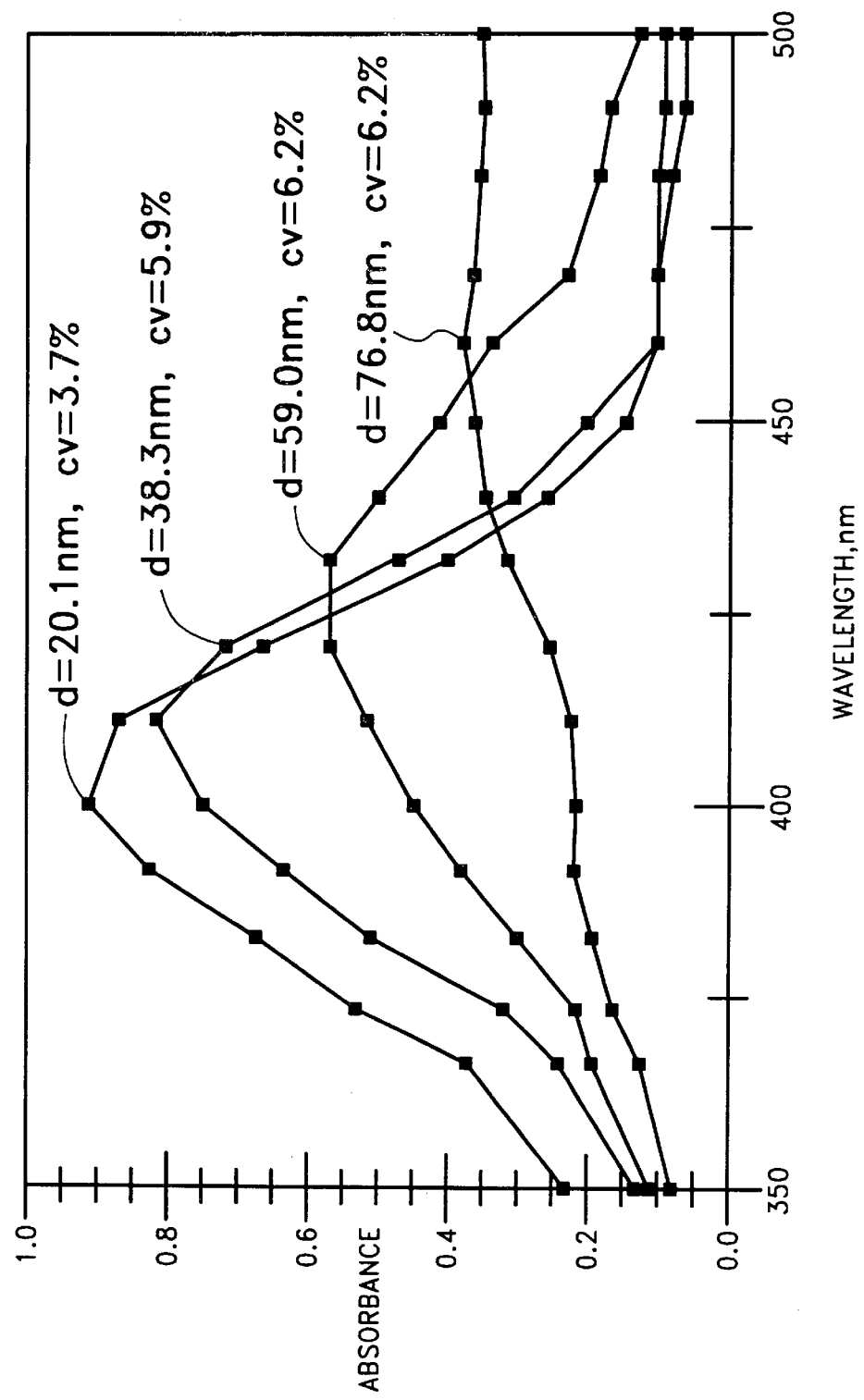
FIG. 5. is a plot showing the effect of particle diameter on optical resonance.

The resonance wavelength is also a function of particle diameter. FIG. 5 shows a series of light transmission spectra of suspensions of silver particles of various diameters taken near the resonance wavelength. It can be seen that, for 20.1 nm diameter particles, the absorption of the sample increases dramatically over a narrow band near 400 nm. The resonance is shifted toward longer wavelengths as the particle diameter increases, and the resonance becomes less sharply peaked and more dispersed over a wider wavelength band. For example, with 76.8 nm diameter particles, the resonant wavelength has moved out to about 460 nm and the resonance is about one third as strong as for 20.1 nm particles.

Figure 6:
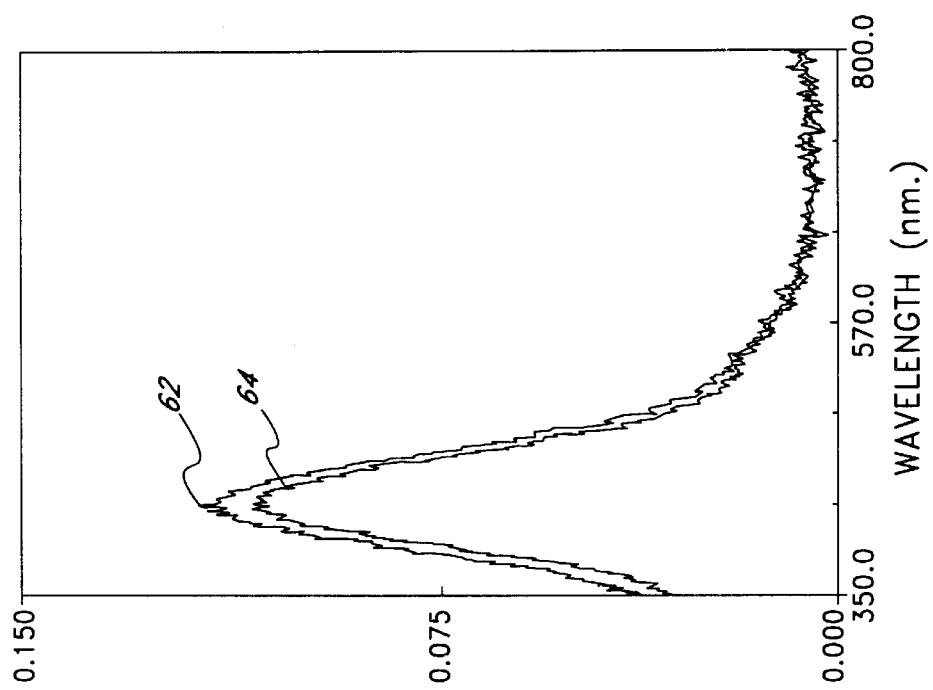
FIG. 6. is a plot showing the effect on optical resonance of coating the resonant particles with protein.

The silver particles were then coated with the binding protein streptavidin (MW 65,000). Coating was performed by passive adsorption at room temperature. For the purpose of protein coating an aqueous solution of colloidal silver particles was first diluted with Tris/HCl buffer, pH 9.0 to an optical absorbance at the resonant wavelength peak of 1.1 absorbance units, thereby achieving a final buffer concentration of 200 mM Tris/HCI. Streptavidin was added to a concentration of 0.1 µg/ml and incubated for 20 min at room temperature. Spectrophotometric measurements were taken before the addition of protein and 20 min after the addition of protein. For purposes of absorption reading both samples were diluted 1:10 with 200 mM Tris/HCI buffer, pH 9.0. FIG. 6 shows the particle absorption resonance 62 before and after 64 protein coating. The Streptavidin perturbs the resonance by shifting the absorption peak very slightly to a longer wavelength and lowers the absorption maximum.

Figure 7:
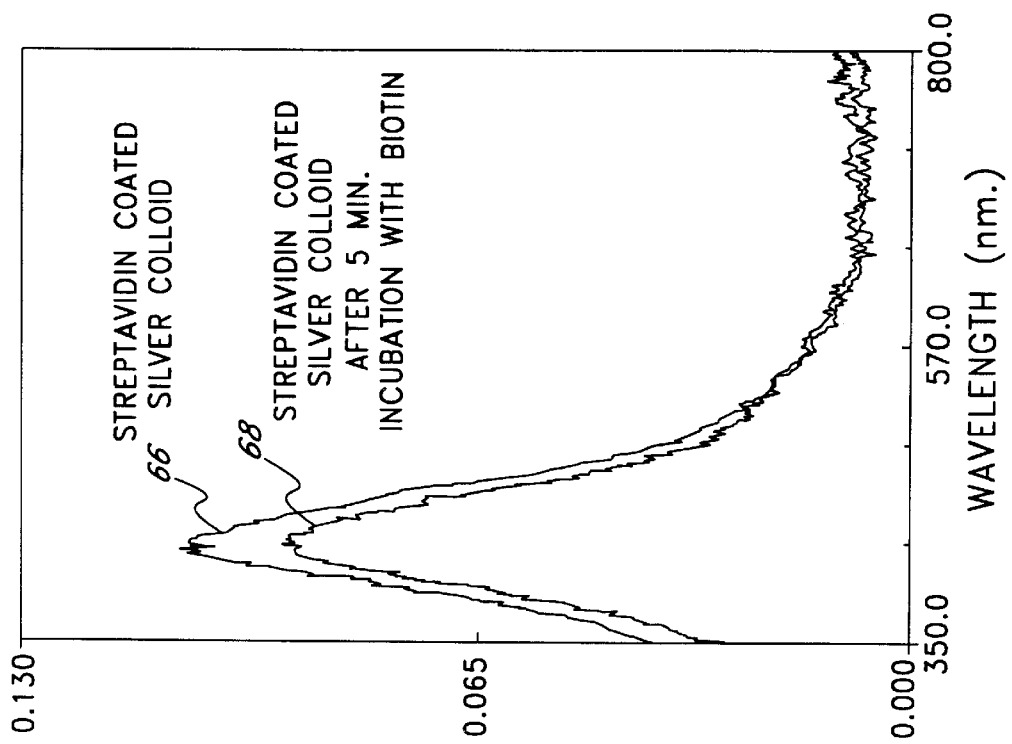
FIG. 7. is a plot showing the effect on optical resonance of the binding of unlabelled ligand to resonant particles.

When Streptavidin-coated particles were later contacted with a solution of biotin, the resonance peak was observed to decrease over time. FIG. 7 is an absorption spectrum 68 taken five minutes after the Streptavidin coated particles were contacted with an aliquot of a solution containing 10 ng/ml of biotin (MW 100). The binding reaction was essentially complete within five minutes. The time course of biotin binding can be measured directly in the reaction mixture. This is compared with an absorption spectrum 66 of the particles prior to the addition of biotin (this sample was pre-diluted with an aliquot of buffer equal to the later biotin addition to correct for dilution effects.

The decrease in the resonant absorption peak after five minutes of binding is a function of the biotin concentration as shown in the table below.

| Biotin Concentration | Absorbance Decrease |
| --- | --- |
| 1 nanograms/ml | 0.002 absorbance units decrease |
| 3 nanograms/ml | 0.010 absorbance units decrease |
| 10 nanograms/ml | 0.015 absorbance units decrease |

These Streptavidin-coated particles were tested for specificity by contacting them with other small molecules that do not bind to Streptavidin. In all cases, the absorbance change was less than 0.001 absorbance unit up to concentrations of 10 micrograms/ml.

In a second test, the solution phase hapten rhodamine was used with a murine anti-rhodamine antibody immobilized on the silver particles. The observations of a similar decrease in optical absorbance over a similar time were repeated, indicating that the molecular weight and size differences between Streptavidin and mouse immunoglobulin do not significantly affect the outcome of the experiment.

Other methods of immobilizing biomolecules on the surface of the silver or other resonant colloidal particles are possible. Large numbers of bifunctional or polyfunctional organic molecules with reactive groups for attaching biomolecules to solid surfaces are well-known to those of skill in the art. These reactive groups include aldehydes, isocyanates, isothiocyanates, and succinimidyl esters among others. Besides simple absorption self-assembling monolayers can also be used to provide functional groups at a metal surface that are useful in immobilizing receptors. Receptors that are isolated from cells can also be immobilized together with fragments of cell membrane in which the receptors are embedded.

An actual instrument based on the principles of the present invention would include some type of sample handling fluidics and data processing system (computer) as well as the spectrophotometers described above. For example, in a screening of a chemical library looking for a new therapeutic drug an aliquot of each compound to be screened could be placed in one well of a multi-well titer plate. An automatic indexing system would move the plate to advance each well into the analyzing beam of a spectrophotometer as defined above. As the well advances into the analysis position an automatic pipetting system dispenses an aliquot of colloidal particles into the well. The particles have on their surfaces the receptor with which the candidate drug is to interact. The pipetting system or some other automatic device insures that the particles and the test compound are thoroughly mixed. The spectrophotometer then measures any changes at the resonant peak as an indication of binding. Preferably these measurements take place over a few minutes so that a time course of binding can be determined. The computer receives this data and calculates the results for each candidate compound. The device then moves on to the next well. If binding is measured over a five minute period, 12 sample compounds can be analyzed per hour. If the test period is shorter, a larger number can be screened. An instrument can be preloaded with dozens of plates so that analysis can proceed day and night without human intervention. The instruments are small and fairly economical so that a plurality of instruments can operate in parallel to screen thousands of candidate compounds in a 24 hour period. Of course, many test variations are possible. By including a known ligand for the receptor one can screen for competition or inhibition by the test compound.

In addition to the equivalents of the claimed elements, obvious substitutions now or later known to one with ordinary skill in the art are defined to be within the scope of the defined elements. The claims are thus to be understood to include what is specifically illustrated and described above, what is conceptually equivalent, what can be obviously substituted and also what essentially incorporates the essential idea of the invention. Therefore, it is to be understood that, within the scope of the appended claims, the invention may be practiced other than as specifically described herein.

We claim:

1. A method for determining binding of a ligand comprising the steps of:

providing colloidal particles having a complex index of refraction and showing optical resonance at a resonant wavelength, said particles coated with a receptor for the ligand, wherein the resonant wavelength is a wavelength at which a real part $n(\lambda)$ of the index of refraction approaches zero while an imaginary part $n(\lambda)$ of the index of refraction simultaneously approaches $\sqrt{2}$, and wherein diameter of said particles is less than about $\frac{1}{10}$ of the resonant wavelength;

contacting the colloidal particles with a sample solution; and measuring light scatter and/or light absorption at the resonant wavelength whereby a decrease in light scatter and/or light absorption at the resonant wavelength is representative of binding of the ligand to the colloidal particles.

* * * * *